United States Patent [19]
Semenov et al.

[11] Patent Number: 4,595,017
[45] Date of Patent: Jun. 17, 1986

[54] METHOD FOR AUTOMATIC PROCESSING OF ELECTRO-OCULOGRAPHIC

[75] Inventors: Pavel A. Semenov; Svyatoslav N. Fedorov; Emilia M. Mironova; Eleonora V. Egorova; Alexandr A. Karavaev, all of Moscow, U.S.S.R.

[73] Assignee: Moskovsky Nauchno-Issledovatelsky Institut Mikrokhirurgii Glaza, Moscow, U.S.S.R.

[21] Appl. No.: 713,996

[22] Filed: Mar. 20, 1985

[30] Foreign Application Priority Data
Apr. 2, 1984 [SU] U.S.S.R. ............................. 3718819

[51] Int. Cl.⁴ .............................................. A61B 5/04
[52] U.S. Cl. ................................... 128/733; 128/745; 364/417
[58] Field of Search ................. 128/733, 745; 364/417

[56] References Cited
U.S. PATENT DOCUMENTS

| | | | |
|---|---|---|---|
| 3,000,271 | 9/1961 | Harvey et al. | 128/745 |
| 3,657,646 | 4/1972 | Zmyslowski et al. | 128/733 |
| 3,774,593 | 11/1973 | Hakata et al. | 128/733 |
| 4,131,113 | 12/1978 | Fender et al. | 128/745 |
| 4,155,352 | 5/1979 | Toglia et al. | 128/745 |

OTHER PUBLICATIONS

Magora et al, "Electromyography and Clinical Neurophysiology", v. 16, No. 6, Dec. 1976, pp. 637–643.
Lubonsky, "IEEE Transactions on Biomedical Engineering", v. BME-24, No. 5, Sep. 1977, pp. 461–466.

Primary Examiner—William E. Kamm
Attorney, Agent, or Firm—Lilling & Greenspan

[57] ABSTRACT

A method for automatic processing of electro-oculographic signals consists in carrying out visual stimulation of a patient at a preset stimulation angle and within a preset period of time, recording the signal of the bioelectric potention of the patient's eye, amplifying said bioelectric potential signal and limiting its spectrum, measuring the amplitude of the bioelectric potential signal at preselected instants of time, and subjecting the thus-measured values of the amplitude of said signals to statistical analysis to determine a constant electro-oculographic eye potential. The time instants at which the amplitude is measured are selected by determining the global extreme values of an absolute magnitude of the bioelectric potential within a preset number of stimulation cycles, comparing the modules of the thus-fixed global extreme values to one another and comparing the time intervals between the fixed global extreme values with the stimulation period.

1 Claim, 6 Drawing Figures

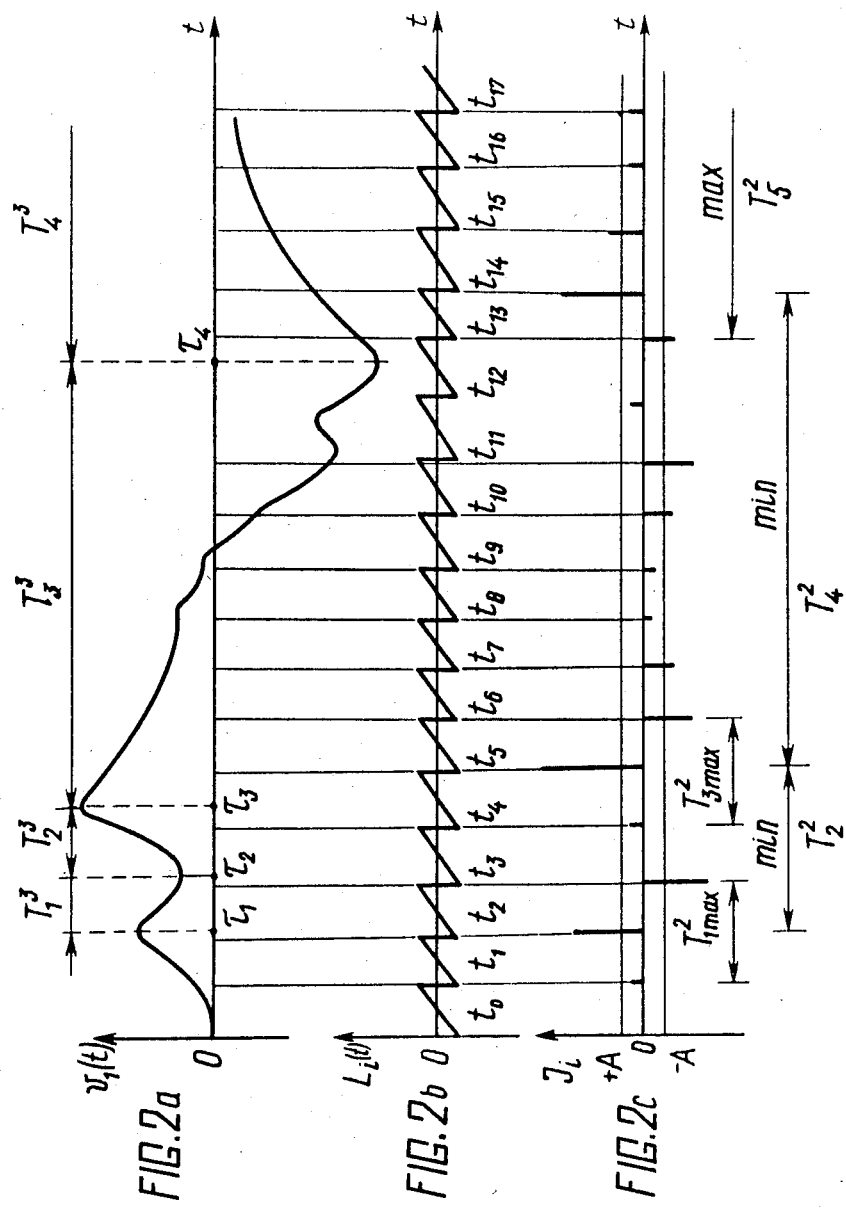

METHOD FOR AUTOMATIC PROCESSING OF ELECTRO-OCULOGRAPHIC

FIELD OF APPLICATION

The invention relates generally to medical instrument-making industry and more specifically, to a method for automatic processing of electro-oculographic signals. The invention can find application in developing automatic electro-oculographic (EOG) measuring and diagnostic equipment.

BACKGROUND OF THE INVENTION

Known in the present state of the art is a method for semiautomatic processing of electro-oculographic signals (cf. Mode. 7310/7102/7402 Operating Manual. Life-Tech. Instruments, Houston, Tex.; Cadwell 5200. Archives of Ophthalmology, 1983, vol. 101, No.3, p.345; Cadwell 7400. Archives of Ophthalmology, 1983, vol. 101, No.4, p.549), consisting in visual stimulation and storing of the input bioelectric (action) potential in the memory of the apparatus, or its taking down by a recorder. According to the method, the measurement results are obtained by extracting the bioelectric potential signal from the memory, displaying it graphically as a curve on a screen, tracing a videomarker along the displayed curve and fixing the bend points of the signal curve, while spurious signals are filtered out by the operator himself.

The method in question involves direct participation of man in recording an electro-oculogram and isolating intelligence electro-oculographic signals from the recorded input signal, as well as requires much time to be spent by the operator.

Another method for automatic processing of electro-oculographic signals is known (cf. "Pulse electro-oculography—a new objective method of clinical electro-oculography" by V. Ya. Eskin and D. I. Kaplunovich, Vestnik oftalmologii, 1983, No. 4, p.6 (in Russian), wherein an electro-oculographic potential is represented as the ratio of the maximum rate of rise of an input signal of action potential to the weighted mean value (or the value measured by some other method) of the maximum angular rate of eyeball rotation.

Such a method is featured by a considerable loss of accuracy of every particular measurement in case of division by the weighted mean value of the maximum angular rate of eyeball rotation. In addition, the result obtained depends upon the angle of eyeball rotation, since the derivative of the input signal is the function of the angle of eyeball rotation. Furthermore, the method involves additional determination of a specific value of the maximum angular rate of eyeball rotation.

One more method for automatic processing of electro-oculographic signals consists in integrating a bioelectric potential drawn from a patient within a preset lapse of time (cf. M. J. Holland, F. Clark. An automatic measuring and recording system for clinical electro-oculography. Ophthal. Res., v.3, p.311–319, 1972).

However, this method also suffers from a badly affected accuracy of results obtained due to long-time erroneous gaze shifting.

Known heretofore is a method for automatic processing of electro-oculographic signals (cf. Jackson S. A. Automated electro-oculography—a microprocessor application example, J. of Medical Eng. & Technology, v.4, No. 6, 1980, p.285–289), consisting in visual stimulation with the aid of a ruler composed of 32 light stimuli whose changing-over should be traced visually by the patient, recording the five values of the action potential signal amplitude, followed by processing said values with a view to selecting any three of them falling within the framework of a preset aperture, averaging said values and normalization to the angle of eyeball rotation to obtain a constant electro-oculographic potential of the eye.

The method under consideration is characterized by:
complicacy of visual stimulation;
necessity of bringing visual stimulation in synchronism with patient's gaze shifting;
susceptibility of the results to various disturbances, such as erroneous gaze shifting, particularly on account of a possibility of selecting three amplitude values through falling within the frame of the aperture but proving to be erroneous (which may be the case with low amplitude values and a large aperture).

A method for automatic processing of electro-oculographic signals (cf. Pantops 500. Mode d'Emploi. Schlumberger Instruments et Systémes) is in fact the one most resemblant to the method of the present invention. This prior-art method resides in subjecting the patient to visual stimulation at a preset angle and within a preset period of time, recording the action potential signal of the patient's eye, amplifying said signal, limiting the spectrum of said action potential signal, measuring the amplitude of the action potential at preselected instants of time, and processing the measurement results to obtain a constant electro-oculographic constant of the eye. The preselected time instants at which the amplitude of the action potential is measured are referred strictly and invariably to the numbers of stimulation cycles from the very beginning of measurements and correspond to the midpoints of the time intervals between each change-over of the visual stimuli. Four amplitude values are fixed, i.e., those corresponding to the gaze at the right, at the centre, at the left and at the centre again. The amplitude values thus obtained are then displayed on a CRT screen and measured manually by the operator. There is assumed as an informational value a difference between the amplitude value corresponding to the gaze at the right and left and that corresponding to the gaze at the centre. A constant electro-oculographic potential results from normalization of the thus-obtained deviation of the amplitude value to the angle of eyeball rotation (or to the sinus thereof).

The method discussed above, however, suffers from the following disadvantages:
low accuracy of results obtained, since the measurement process makes no provision for isolating the intelligence electro-oculographic signals from the whole input signal in which signals caused by nystagmoid eye movements, nictitation, etc. are present;
reliable and trustworthy results are attainable only when complete synchronism of visual stimulation and patient's gaze shifting is provided, which cannot be observed in a majority of cases.

OBJECT AND SUMMARY OF THE INVENTION

It is an object of the invention to provide a higher accuracy of measurements.

It is another object of the invention to make the measurement results less sensible to various disturbances.

The essence of the invention resides in that in a method for automatic processing of electro-oculographic signals, consisting in visual stimulation of a patient at a preset angle and within a preset period of time, recording the bioelectric potential signal of the patient's eye, amplifying said signal, limiting the spectrum of said bioelectric potential signal, measuring the amplitude of the bioelectric potential signal at preselected instants of time, and processing the measured values of the amplitude of the bioelectric potential signal to determine a constant electro-oculographic potential of the eye, according to the invention, the instants of time at which the amplitude of the bioelectric potential signal is measured, are selected by determining the global extreme value of an absolute magnitude of the bioelectric potential within a predetermined number of stimulation cycles, shaping a signal representing a functional threshold associated with said global extreme value via a nondecreasing functional relationship, dividing the entire measurement process that follows into a sequence of first equal time intervals within each of which an integral signal $I_i$ is shaped according to the following relation:

$$I_i = \int_{t_i}^{t_{i+1}} L_i(t)U(t)dt.$$

where
t—running time ($t\epsilon[t_i, t_{i+1}]$);
$t_i$—the left-hand bound of the running i'th first time interval;
$t_{i+1}$—the right-hand bound of the running i'th first time interval;
V(t)—spectrum-limited bioelectric potential signal,
$L_i(t)$—linearly varying signal symmetrical with respect to zero within the running time interval [$t_i$, $t_{i+1}$], whereupon the resultant integral signal $I_i$ is compared with the functional threshold signal and a second time interval is isolated which is bounded respectively by the left- and right-hand bounds of the first time intervals corresponding to the first time instants when the module of the integral signal $I_i$ exceeds the functional threshold signal (provided that the sign of the integral signal is reversed), then the running global extreme value of the bioelectric potential signal is determined within said second time interval along with the instant at which said signal reaches said value, after which a third time interval is isolated between two adjacent global extrema and compared with the stimulation period and, if every third time interval between the adjacent global extrema of the bioelectric potential approximates to the stimulation period, a preset number of the sequential running global extrema are fixed, whereupon said fixed global extreme values of the biolectric potential signal are compared with one another and, if closely approximating, no further measurements are carried out, the thus-fixed values of amplitudes of the global extrema are subjected to statistical analysis after which a constant electro-oculographic potential of the eye is determined; if the aforestated condition of similarity between the third time intervals and the stimulation period, or that between the global extreme bioelectric potential values fail to be met, the amplitudes of the bioelectric potential signals continue to be measured until all the aforementioned conditions are fully met within a preset number of stimulation cycles; if only the condition of similarity between the fixed values of amplitudes of the global extrema cannot be satisfied, so nonequiangular visual fixation is inferred; when only the condition of similarity between the third time intervals and the stimulation period fails to be met, the automatic processing is repeated with the intensity of the functional threshold signal gradually increased; if the intensity of the functional threshold signal reaches a preset limiting value, so inference is to be drawn that a constant electro-oculographic eye potential is undeterminable in this particular case.

The method for automatic processing of electro-oculographic signals carried into effect in accordance with the present invention, enables one to substantially increase the accuracy of measurement and enhance the confidence and reliability of determining a constant electro-oculographic eye potential, and also to render the present diagnostic technique fully automated. This in turn makes it possible to cut down the attending personnel eight times when the present method finds mass-scale application.

Moreover, practical application of the present method reduces the processing time of the EOG signals by about 25 percent, since the measurement results can be processed automatically at a high rate.

BRIEF DESCRIPTION OF THE DRAWINGS

In what follows the invention will now be disclosed in a detailed description of illustrative specific embodiments thereof with reference to the accompanying drawings, wherein according to the invention:

FIG. 2a represents a change in time t of an input signal $U_1$ of bioelectric potential after its amplification and spectrum limiting, and third time intervals $\{T_k^3\}$;

FIG. 2b represents first time intervals $\{t_i\}$ and a voltage signal $L_i$ linearly variable within the time intervals $\{t_i\}$;

FIG. 2c represents a change in time t of an integral signal $I_i$ as taken at the end points of the first time intervals $\{t_i\}$, and second time intervals $\{T_k^2\}$;

DETAILED DESCRIPTION OF THE INVENTION

The method for automatic processing of electro-ocular signals disclosed in the present invention, resides in the following. Before starting a cycle of measurements, one should set a visual stimulation period $T_s$ and a stimulation angle $\rho$ equal to the angle of eyeball rotation when patient's gaze is shifted from one light stimulus to another. The input bioelectric eye potential is recorded with the aid of bioelectric potential sensors placed at the internal and external canthi.

Next the thus-recorded bioelectric potential signal is amplified and applied to frequency cut-off filters which limit the spectrum of the signal. The upper frequency limit of the filters is equal to a maximum frequency of the EOG signal spectrum, while the lower frequency limit either equals zero or approximates it. In further consideration the lower frequency limit (or limiting frequency) is assumed to be, e.g, $f_1 \simeq 1/3T_s$, which makes it possible to "peak" the extreme points of the signal instrumentally so as to render the instants of gaze shifting more clearly discriminable. All described hereinafter holds true for the case when $f_1 << 1/T_s$, wherein an output signal of the filters is in fact a train of square pulses.

Then the amplitude of the spectrum-limited bioelectric potential signal is measured at the time instants whose selection is determined by the following sequence of operations.

A global extreme value of an absolute magnitude $|U|_{max}$ of the bioelectric potential is determined within a preset number (usually from one to twenty) of stimulation periods, said extreme value (hereinbelow referred to as extreme) being used for shaping a functional threshold signal FT. An optimum number of the stimulation periods is four or five, since in this case adequately high reliability of assessment of the global extremum is attained, while the patient's oculomotor system has no time enough to get fatigued and can thus fix patient's gaze precisely. It is the same periods that are utilized for "training" the patient and his/her synchronization with switching-over of the visual stimuli.

The functional threshold signal FT is used for an automatic tuning of an EOG signal discrimination system for a specific bioelectric potential signal. The signal FT is associated the global extremum of the module $|U|_{max}$ via a nondecreasing monotonous relationship. The thus-formed functional threshold signal FT remains invariable during the entire next measurement cycle and is used for suppressing noise resulting from nictitation, turns of the head, etc., as well as for eliminating nonintelligence local extrema of a low-amplitude bioelectric potential.

Figure 1:
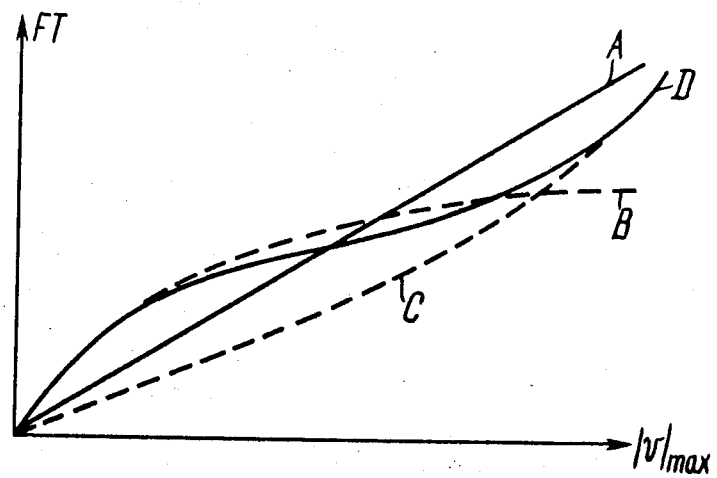
FIG. 1 illustrates exemplary graphic representations of a functional threshold signal FT versus a global extreme value of the module $|U|_{max}$ of a bioelectric potential signal.

A variety of relations $FT(|U|_{max})$ are possible as represented in FIG. 1:

Relation A:

$$\frac{d(FT)}{d(|U|_{max})} = \text{const} \quad (1)$$

Relation B:

$$\lim_{|U|_{max} \to \infty} \frac{d(FT)}{d(|U|_{max})} = 0 \quad (2)$$

Relation C:

$$\lim_{|U|_{max} \to \infty} \frac{d(FT)}{d(|U|_{max})} = \infty \quad (3)$$

Relation D:

$$\left. \frac{d^2(FT)}{d(|U|_{max})^2} \right|_{|U|_{max}=\min} \cdot \left. \frac{d^2(FT)}{d(|U|_{max})^2} \right|_{|U|_{max}=\max} < 0 \quad (4)$$

The linear relation (1) meets the condition of stability of a relative noise level (nictitation, erroneous gaze shifting, etc.) with respect to the desired signal level for all patients whatever the value of a constant eye potential. In such a case the ratio of the maximum value of an integral signal (see below) to the functional threshold value is approximately constant for all patients, and therefore a constant relative threshold is employed as the signal detection criterion. Such a relationship is retained within a group of patients featuring a narrow spread of the constant eye potential value.

The relation (2) corresponds to a maximum "saturation" occurring in response to an increase in the value of $|U|_{max}$. This holds true also for going from a domain of low values of constant eye potential to that of normal values thereof, characterized by the absence of retinopathies "visible" (i.e., detectable) by electro-oculography.

The relation (3) corresponds to a transition from the domain of normal constant eye potential values to that of supernormal values, with which some pathological conditions are possible. In such a case the noise level increases and the functional threshold should be increased accordingly.

The relation (4) corresponds to a sign reversal of the second derivative within a range of possible changes in constant eye potential (from $|U|_{max}=\min$ to $|U|_{max}=\max$) and integrates all the three aforedescribed relations showing the dependence of the functional threshold upon the value of the global extremum of the module $|U|_{max}$ of the bioelectric potential. Such a relation features the best properties for detecting an EOG signal. Examples of such relations are $shk(x-a)$; $k(x-a)^{2b+1}$; arcsin $k(x-a)$, and so on, where x—dependant variable; k, a, b—coefficients and parameters.

Inasmuch as the most considerable changes of the relative threshold occur in the region of low values of constant eye potential, wherein there is exhibited also a negative effect of amplifier and quantization noise accompanying the digital realization of the method, so good properties are possessed also by the relations (2) to which pertain: ln $k(x+a)$; $x^\alpha(0<\alpha<1)$; $thk(x+b)$, and the like, where x—a variable; k, $\alpha$, a, b—coefficients and parmeters.

The coefficients and parameters of a functional relationship $FT(|U|_{max})$ are determined proceeding from optimum conditions for detecting an intelligence EOG signal against a background of the aforementioned noise and erroneous gaze shiftings. The best optimality criterion in a given case is the Neumann-Pierson criterion which provides for the maximum probability of correct detection with a limited maximum probability level of "false alarm". It is due to changing the coefficients and increasing the value of FT when no series of "regular" (normal) extrema of bioelectric signal is found to follow a preset number of stimulation cycles (see below) that the probability of a "false alarm" is reduced and the detection conditions in bad eyesight patients are "weakened".

It must be pointed out that with a view to simplifying instrumental realization of the method use may be made of various types of approximation of the afore-described relations, in particular, piecewise-linear and step-by-step approximations.

Figure 3:
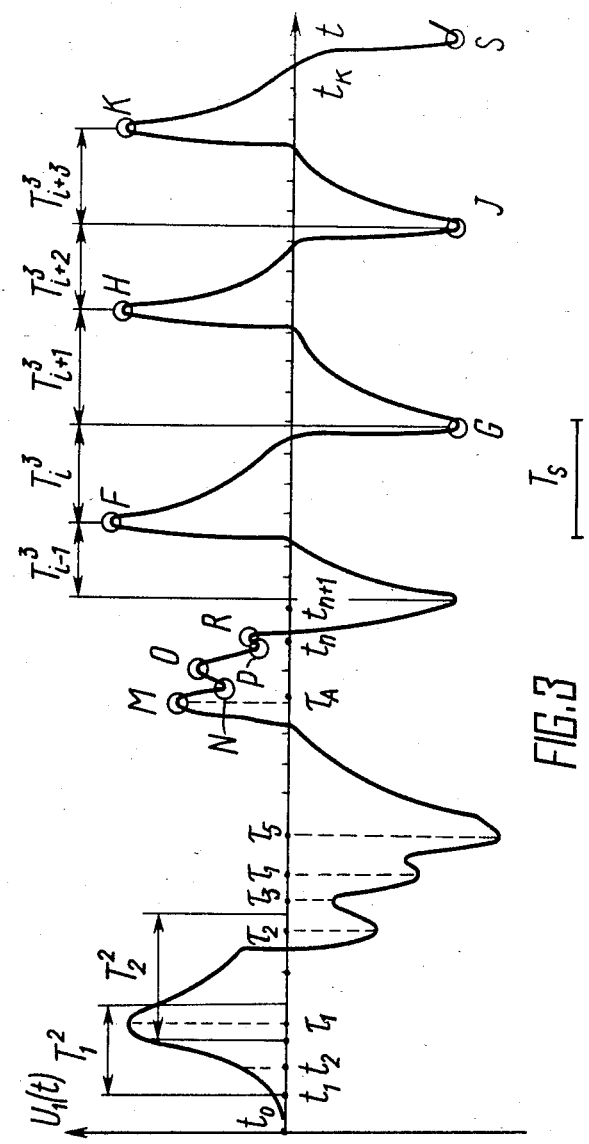
FIG. 3 illustrates an exemplary graphic representation of an input signal $U_1(t)$ of bioelectric potential as processed in accordance with the method of the present invention.

Then the entire measurement cycle is divided into a sequence of first constant time intervals $\{[t_i, t_{i+1}]\}$ ($t_0, t_1, t_2 \ldots t_i, t_{i+1}$) FIG. 2b, FIG. 3). Next a signal $L_i(t)$ is shaped within each of the time intervals $[t_i, t_{i+1}]$, which signal is associated with the running time t by a linear functional relationship symmetrical with respect to zero within the time interval $[t_i, t_{i+1}]$ (FIG. 2b). Such a relationship can be exemplified as follows: $L_i(t) = 2t - t_i - t_{i+1}$.

Any other linear relationship $L_i'(t)$ satisfying the aforementioned conditions can be expressed through $L_i(t)$:

$$L_i^1(t) = \alpha L_i(t) \quad (5)$$

where α—constant factor (α 0).

Here and hereinafter the term 'linearly variable signal' implies, e.g., the signal $L_i(t)$.

Next an integral signal $I_i$ is shaped within each time interval $[t_i, t_{i+1}]$:

$$I_i = \int_{t_i}^{t_{i+1}} L_i(t) U(t) dt \tag{6}$$

where $U(t)$—spectrum-limited bioelectric potential signal (FIG. 2a).

On termination of each running time interval $[t_i, t_{i+1}]$ the thus-shaped integral signal $I_i$ is compared with the aforementioned functional threshold signal FT (FIG. 2c).

Thereupon a first time instant $t_i$ is fixed provided that the absolute value (magnitude) of the integral signal $I_i$ exceeds the intensity of the functional threshold signal FT within the time interval $[t_i, t_{i+1}]$ (a time instant $t_1$ in FIG. 2c).

A time instant $t_{j+1}$ is fixed in a similar way provided that the magnitude of the integral signal $I_j$ exceeds the intensity of the functional threshold signal FT within the time interval $[t_j, t_{j+1}]$ for the first time after the time interval $[t_i, t_{i+1}]$, and the sign of the integral signal is opposite to its sign within the time interval $[t_i, t_{i+1}]$ (a time instant $t_3$ in FIG. 2c). A sequence of such first time instants establishes the second time intervals $T_k^2$, $T_1^2$, $T_2^2$, and so on as shown in FIG. 2c).

Next the global extremum of a bioelectric potential signal obtained after spectrum limiting, is determined within each of the time intervals $T_k^2$. The type of the blobal extremum depends on the sign of the integral signal $I_i$ within the second running time interval $T_k^2$ (assuming that $I_i<0$—the minimum, $I_i>0$—the maximum, with $\alpha>0$ in formula (5).

Next there are isolated time instants $\tau_k$ pertaining to the respective second time intervals $T_k^2$ ($\tau_k \epsilon T_k^2$) and corresponding to the instant when the spectrum-limited bioelectric potential signal reaches its global extrema within the time interval $T_k^2$ (FIG. 2a).

Then a series of third time intervals $\{T_1^3, T_2^3 \ldots T_k^3\}$ are formed from a sequence of time samples $\{\tau_1, \tau_2, \ldots \tau_k, \ldots\}$, wherein $T_i^3$ (FIG. 2a) is defined as a time interval between time instants $\tau_i$ and $\tau_{i+1}$ corresponding to the instant when the spectrum-limited bioelectric potential signal reaches its adjacent global extrema within the second adjacent time intervals $T_i^2$ and $T_{i+1}^2$, i.e., $T_i^3 = \tau_{i+1} - \tau_i$.

Thereupon there is accumulated a predetermined number n (as a rule n=2 to 10) of the end consecutive global extrema of the spectrum-limited bioelectric potential signal provided that the relationship of similarity between the stimulation period $T_s$ and the third time intervals $T_i^3$ corresponding to each of the aforestated global extrema of the bioelectric potential signal is satisfied. Applied as such a similarity relationship may be, e.g., the following condition:

$$T_i^3 \epsilon [T_s(1-\delta), T_s(1+\delta)] \tag{7}$$

where
$T_i^3$—the i'th time interval of the third type;
$T_s$—stimulation period;
$\delta$—the parameter of similarity interval width.

The parameter δ is selected proceeding from a possible nonuniform time lag of patient's gaze shifting to the opposite sides in response to changing-over the light stimuli. For a majority of patients the non-uniformith value of such time lags is within 0.5 $T_s$; hence $\delta \leq 0.5$.

In the given particular case as represented in FIG. 3 the relationship (7) is not satisfied for extreme points M, N, O, P, R and is satisfied for extreme points F, G, H, J, K, S.

The number n of the fixed global extrema of a bioelectric potential signal should satisfy the following conditions;

it should be great enough to provide a high probability value of said extrema belonging to a series of correct (intelligence-giving) gaze shiftings at a preset stimulation angle with the time intervl $T_s$;

it should be as low as not to fatigue the patient's oculomotor system, since in such a case an occasional gaze shifting might occur resulting in a "break-down" of sequential EOG-signal discrimination and in a loss of all the accumulated values of the extrema, whereby the probability value of discriminating a sequence of intelligence-giving gaze shiftings of a preset time length becomes minimized even in patients featuring normal gaze fixation.

Further on, once the aforestated number n of the global extrema $U_i$ (i=1 to n) has been accumulated, said extrema are checked for similarity between their absolute values $U_i$ (i=1 to n). Used as a similarity criterion may be, e.g., any one of the relations given below:

$$\sigma_1 = \frac{\underset{i}{MAX}\{|U_i|\} - \underset{i}{MIN}\{|U_i|\}}{\underset{i}{MAX}\{|U_i|\}} \leq \sigma_1^{max} \tag{8}$$

$$\sigma_2 = \frac{\underset{i}{MAX}\{|U_i|\} - \underset{i}{MIN}\{|U_i|\}}{\underset{i}{MIN}\{|U_i|\}} \leq \sigma_2^{max} \tag{9}$$

$$\sigma_3 = \frac{\underset{i}{MIN}\{|U_i|\}}{\underset{i}{MAX}\{|U_i|\}} \leq \sigma_3^{max} \tag{10}$$

$$\sigma_4 = \frac{\sqrt{n \sum_{i=1}^{n} U_i^2 - \left(\sum_{i=1}^{n} |U_i|\right)^2}}{\sum_{i=1}^{n} |U_i|} \leq \sigma_4^{max} \tag{11}$$

where
$_i MAX \{x\}$—the maximum value of a sequence $\{x_i\} i=1$ to n;

$_i MIN \{x\}$—the minimum value of a sequence $\{x_i\} i=1$ to n;

n—the number of the global extrema being fixed.

It is the criterion (8) that is to be considered as the most rational, since the criteria (9) and (10) may yield too great values with $_i MIN \{|U_i|\} \approx 0$, while the criterion (11) involves too a great number of operations, which is of no small importance in practical realization of the method.

The parameter $\sigma_m^{max}$ (m=1 to 4) defines the optimum discrimination conditions and depends upon nonuniformity of the bioelectric potential produced in gaze shifting to opposite sides, said nonuniformity amounting to 50 percent in some patients. The aforesaid nonuniformity is either due to asymmetrical (with respect to the optic axis) application of electrodes or due to an unequiangular gaze shifting (which may be the case with strabismus) or also it may be caused by some other pathological conditions. Thus, $\sigma_1$ may assume a magnitude in the range of [0.05].

The condition of similarity between the amplitudes of the extrema is satisfied for points F, G, H, J, K, S in FIG. 3.

Further on, if the condition of similarity between the amplitudes is satisfied, measurements are no longer performed, and the values of the fixed global extrema are subjected to statistical analysis, followed by deriving the results of the analysis for obtaining a constant electro-oculographic eye potential.

For instance, with n=4 the measurement process may be ceased, e.g., at the point J in FIG. 3.

Statistical analysis is required for obtaining reliable assessment of an actual bioelectric potential amplitude corresponding to the eyeball rotation to a preset angle. Employed as a statistical assessment criterion may be, e.g., a mean value or median of the modules $|U_i|$ of the fixed values of the extrema (cf. Two-Dimensional Digital Signal Processing II. Ed. by T. S. Huang. Springer-Verlag Berlin-Heidelberg-N.Y., 1981).

It should be noted that use of the median estimate is preferable, since it is robust with respect to a change in the noise distribution law and to impulse noise. However, the number n of the fixed extrema should in this case be odd.

Next the results of statistical analysis are derived, which may then be normalized to the magnitude of the stimulation angle $\rho$ or to the sinus thereof in order to obtain a constant eye potential value.

Should the aforestated number of extrema fail to be fixed, or the extreme values accumulated fail to satisfy the similarity relationship (relations 8 to 10), the measurement process continues but only within a preset number of cycles. The number of cycles of detection of an intelligence electro-oculographic signal ranges within 20 and 50, which can be explained by a necessity to make it possible to carry out if only one repeated procedure of automatic processing, at a greater functional threshold value, before the beginning of a next dark or light measurement cycle (upper limit), or whenever it is necessary to provide high probability value of detecting a desired signal (lower limit).

Should the criterion of similarity of the amplitudes of the fixed extrema be satisfied, the measurement and stimulation process is discontinued in an appropriate stimulation cycle.

But if both of the aforementioned criteria are not satisfied even after carrying out the specified number of stimulation cycles, the measurement process is discontinued to find out which of the criteria has not been satisfied. If resumption of the measurement process is caused by failure to satisfy the criterion of similarity between the amplitudes of the last fixed extrema, so nonequiangular fixation of patient's gaze is inferred. In such a case the measurement results can be represented, e.g., as the maximum and the minimum amplitudes of the fixed extrema, or as a mean value (median).

Whenever a preset number n of the extrema failed to be accumulated, one should increase the intensity of the functional threshold signal FT and repeat the procedure of automatic processing of EOG signals while the intensity of the functional threshold signal is increased gradually and incessantly, thereby trying to satisfy all the aforementioned criteria. However, when the measurement results fail to be fixed in this case, too, whereas the functional threshold signal has already reached its preset level, the measurement process is to be discontinued and inference is to be drawn that a constant electro-oculographic eye potential cannot be determined in this particular case.

It is by increasing the intensity of the functional threshold signal FT that noninformative occasional shifts of patient's gaze can be "neglected", whereby "false alarm" becomes less probable when the Heumann-Pirson detective criterion is applied.

The maximum functional threshold value at which one must infer that a constant electro-oculographic eye potential cannot be determined is usually two to twenty times its initial value.

Figure 4:
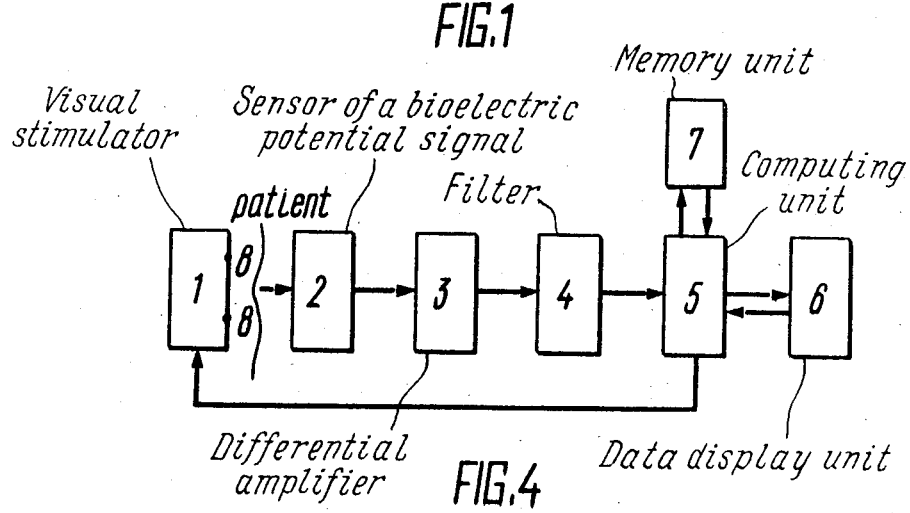
FIG. 4 is a block diagram of a device for carrying into effect a method for automatic processing of electro-oculographic signals.

FIG. 4 represents a block diagram of a device for carrying into effect the method for automatic processing of EOG signals, according to the invention.

The device comprises a visual stimulator 1, sensors 2 of a bioelectric potential signal and series-connected a differential amplifier 3, a filter 4, a computing unit 5 and a data display unit 6, all these being connected to the input of the sensors 2. In addition, a memory unit 7 is connected to the computing unit 5.

The patient is placed in front of the visual stimulator 1. The sensors 2 are placed at the internal and external canthi and are in fact contact lamels coated with an Ag-AgCl compound (cf. Polygraph system planning manual. Nikon Kohden, Tokyo, Japan). The visual stimulator 1 comprises visual stimuli 8 (usually microlamps or light-emitting diodes) and illumination circuits to provide a possibility of taking measurements in the light phase (cf. Arden G. B., Barrada A., Kesley J, "Brit. J. Ophthal." 1962, 46, 8 p.449–467). As a rule, the stimulation light-emitting diodes are spaced an angular distance $\rho = 10°$ to $40°$ apart from patients eye ($\rho$ being the stimulation angle), and are turned on alternately at a time interval equal to the stimulation period $T_s$ (usually $T_s = 0.5$ to 2.0 s).

The patient should trace visually the changing-over of the light stimuli 8 and fix his/her gaze firmly.

Upon intensifying the bioelectric potential signal in the differential amplifier 3 and limiting its spectrum by the filter 4, the signal arrives at the computing unit 5 which is connected to the memory unit 7 and the data display unit 6 and is adapted to control the switching-over of the visual stimuli 8 in the visual stimulator 1.

The functioning process of the device begins with determination of the maximum value of an absolute magnitude of a bioelectric potential signal by the computing unit 5 within, e.g., 5 stimulation cycles, followed by formation of a value of the functional threshold FT. Then the computing unit 5 changes to a mode of detecting an EOG-signal corresponding to first time instants of a dissimilar-polarity gaze shifting (to the right and to the left) by shaping an integral signal $I_i$ (6) within each of the first-type running time intervals $[t_i, t_{i+1}]$ ($\Delta t = t_{i+1} = $ const; and comparing said signal with the intensity of the functional threshold signal FT. Concurrently an extremum $U_j$ and a time instant when said extremum is reached is sought for. The computing unit 5 analyzes the value of $I_i$ at the time instants $\{t_{i+1}\}$. Once the sign of the signal $I_i$ has reversed provided the condition $|I_i| \geq FT$ is satisfied, the type of extremum (min/max) is changed and if the equality ($\tau_j - \tau_{j-1} = T_j^3$) satisfies the criterion (7) of similarity to $T_s$, the value of $U_j$ is remembered in the memory unit 7. Otherwise all the value of $\{U_j\}$ accumulated are lost.

Next the computing unit 5 checks the values of the accumulated extrema for uniformity and makes a decision either to continue to seek for a signal featuring a running value of FT, or to cease measurements and to deliver the measurements results to the data display unit 6, or else to repeat the entire measurement cycle with a higher value of the function threshold FT.

What is claimed is:

1. A method for automatic processing of electro-oculographic signals, comprising the following operations:

visual stimulation of a patient at a preset angle and within a preset period of time;

recording the bioelectric potential signal of the examined patient's eye;

amplifying said signal of the bioelectric potential;

limiting the spectrum of said bioelectric potential signal;

measuring the amplitude of said bioelectric potential signal at preselected instants of time; said preselection of time instants at which the amplitude of the bioelectric potential is measured is carried out as follows:

determining the global extreme value of an absolute magnitude of the bioelectric potential within a predetermined number of stimulation cycles;

shaping a functional threshold signal associated with said global extreme value via a nondecreasing functional relationship;

dividing the entire measurement process that follows into a sequence of first equal time intervals, within each of which an integral signal $I_i$ is shaped according to the following relation:

$$I_i = \int_{t_i}^{t_{i+1}} L_i(t)U(t)dt,$$

where:

t—running time ($t \in [t_i, t_{i+1}]$);

$t_i$—the left-hand bound of the running i-th first time interval;

$t_{i+1}$—the right-hand bound of the running i-th first time interval;

U(t)—spectrum-limited bioelectric potential signal;

$L_i(t)$—linearly varying signal symmetrical with respect to zero within the running time interval $[t_i, t_{i+1}]$;

comparing said integral signal $I_i$ with said functional threshold signal;

isolating a second time interval bounded by the left- and right-hand bounds, respectively, of said first time intervals corresponding to the first time instants when the module of said integral signal $I_i$ exceeds said functional threshold signal provided that the sign of said integral signal is reversed;

determining, within said second time interval, the running global extreme value of said bioelectric potential signal and the time instant when said signal reaches said value;

isolating a third time interval between said two adjacent global extreme values;

comparing said third time interval with said stimulation period;

fixing a preset number of said sequential running global extreme values provided every third of said time intervals between said adjacent global extreme value of the bioelectric potential signal is similar to said stimulation period;

comparing said fixed global extreme values of the bioelectric potential signal with one another;

discontinuing the measurement process of said compared global extreme values of the bioelectric potential signal are similar to one another;

statistical analysis of the fixed values of said amplitudes of the global values of the bioelectrical potential signal;

determining a constant electro-oculographic eye potential;

when the aforestated condition of similarity between said third time intervals and said stimulation period is not satisfied, the process of said measurement of the amplitudes of the bioelectric potential signals continues until all the aforementioned conditions are fully met within not more than a preset number of said stimulation cycles;

when the aforesaid condition of siimilarity between said global extreme values of the bioelectric potential signal is not satisfied the process of said measurement of the amplitudes of the bioelectric potential signals continues until all the aforesaid conditions are fully met within not more than a preset number of said stimulation cycles;

when only said condition of similarity between the values of the amplitudes of the fixed extrema of the bioelectric potential signal cannot be satisfied within said preset number of said stimulation cycles, nonequiangular visual fixation is inferred;

when only said condition of similarity between said third time intervals and said stimulation period is not satisfied, said measurement process is repeated while gradually increasing the intensity of said functional threshold signal;

whenever the intensity of said functional threshold signal reaches a preset limiting value as a result of said gradual increases, inference is made that said constant electro-oculographic eye potential cannot be determined.

* * * * *